United States Patent [19]
Leone-Bay et al.

[11] Patent Number: 5,955,503
[45] Date of Patent: Sep. 21, 1999

[54] COMPOUNDS AND COMPOSITIONS FOR DELIVERING ACTIVE AGENTS

[75] Inventors: Andrea Leone-Bay, Ridgefield, Conn.; Duncan R. Paton, Purdys, N.Y.; Koc-Kan Ho, Mt. Kisco, N.Y.; Frenel DeMorin, Spring Valley, N.Y.

[73] Assignee: Emisphere Technologies, Inc., Hawthorne, N.Y.

[21] Appl. No.: 08/795,833

[22] Filed: Feb. 6, 1997

Related U.S. Application Data

[60] Division of application No. 08/335,148, Oct. 25, 1994, Pat. No. 5,643,957, which is a continuation-in-part of application No. PCT/US94/04560, Apr. 22, 1994, which is a continuation-in-part of application No. 08/051,019, Apr. 22, 1993, Pat. No. 5,451,410, and application No. 08/205,511, Mar. 2, 1994, and a continuation-in-part of application No. 08/231,622, Apr. 22, 1994, Pat. No. 5,629,020.

[51] Int. Cl.$^6$ .............. A01N 37/12; A01N 37/44
[52] U.S. Cl. .............. 514/563; 424/455; 424/489; 424/490; 424/491
[58] Field of Search .............. 514/563, 56; 424/400, 424/455, 489, 484, 464

[56] References Cited

U.S. PATENT DOCUMENTS

| | | |
|---|---|---|
| Re. 24,899 | 11/1960 | Green . |
| 2,671,451 | 3/1954 | Bolger ................................. 128/260 |
| 2,862,918 | 12/1958 | Meyer et al. ..................... 260/123.5 |
| 2,868,740 | 1/1959 | Luce ..................................... 260/8 |
| 2,971,916 | 2/1961 | Schleicher et al. ................ 252/62.5 |
| 3,016,308 | 1/1962 | Macaulay ............................. 177/37 |
| 3,052,655 | 9/1962 | Fox et al. .............................. 260/78 |
| 3,057,344 | 10/1962 | Abella et al. ........................... 128/2 |
| 3,076,790 | 2/1963 | Fox et al. .............................. 260/78 |
| 3,170,802 | 2/1965 | Fukushima ........................... 99/145 |
| 3,190,837 | 6/1965 | Brynko et al. ....................... 252/316 |
| 3,474,777 | 10/1969 | Figge et al. ............................ 128/2 |
| 3,491,093 | 1/1970 | Pachter et al. ..................... 260/247.5 |
| 3,565,559 | 2/1971 | Sato ...................................... 424/37 |
| 3,567,650 | 3/1971 | Bakan ................................. 252/316 |
| 3,574,832 | 4/1971 | Engel et al. ......................... 424/183 |
| 3,576,758 | 4/1971 | Emrick ............................... 252/316 |
| 3,687,926 | 8/1972 | Arima et al. . |
| 3,725,113 | 4/1973 | Chang ................................. 117/82 |
| 3,748,277 | 7/1973 | Wagner ............................... 252/316 |
| 3,794,561 | 2/1974 | Matsukawa et al. ............... 195/29 R |
| 3,795,739 | 3/1974 | Birkmayer et al. ................. 424/274 |
| 3,816,404 | 6/1974 | Kablaoui et al. .................. 260/239.3 |
| 3,822,348 | 7/1974 | Higashi et al. ....................... 424/95 |
| 3,849,550 | 11/1974 | Teitelbaum ........................... 424/78 |

(List continued on next page.)

FOREIGN PATENT DOCUMENTS

| | | |
|---|---|---|
| 1077842 | 8/1976 | Canada ..................... A61K 9/50 |
| 0 000 667 A1 | 2/1979 | European Pat. Off. ......... A61K 9/50 |
| 0 036 145 A1 | 9/1981 | European Pat. Off. ....... A61K 31/62 |
| 0 068 314 | 1/1983 | European Pat. Off. ....... A61K 31/16 |
| 0 105 804 | 4/1984 | European Pat. Off. ........ C12N 15/00 |
| 0 130 162 A2 | 1/1985 | European Pat. Off. ......... B01J 13/02 |
| 0 170 540 A1 | 2/1986 | European Pat. Off. ......... A61K 9/52 |
| 0 342 054 A2 | 11/1989 | European Pat. Off. ......... A61K 7/06 |
| 0 342 056 A2 | 11/1989 | European Pat. Off. ......... A61K 7/06 |
| 0 365 183 | 4/1990 | European Pat. Off. ...... C07C 311/21 |
| 0 366 277 | 5/1990 | European Pat. Off. ....... A61K 9/107 |
| 0 418 642 | 3/1991 | European Pat. Off. ....... A61K 37/30 |
| 0 448 057 | 9/1991 | European Pat. Off. ........ C12P 21/08 |
| 0 452 161 | 10/1991 | European Pat. Off. ......... A61K 7/48 |
| 0 459 795 | 12/1991 | European Pat. Off. ....... A61K 37/02 |
| 0 467 389 | 1/1992 | European Pat. Off. ......... A61K 9/52 |
| 0 490 549 A1 | 6/1992 | European Pat. Off. ....... A61K 47/12 |
| 0 517 211 A1 | 9/1992 | European Pat. Off. ....... A61K 47/12 |
| 0 616 799 A1 | 9/1994 | European Pat. Off. ......... A61K 7/00 |
| 1 351 358 | 3/1964 | France . |
| 1 468 601 | 2/1967 | France . |
| 2 133 926 | 12/1972 | France .......................... A61K 27/00 |

(List continued on next page.)

OTHER PUBLICATIONS

Airaudo, C.B. et al. (1987) *Journal of Food Science*, vol. 52(6), pp. 1750–1752.
Andini, S. et al. (1975) *Origins of Life*, vol. 6, pp. 147–153.
Brooke, S. 1 et al. (1977) *BioSystems*, vol. 9, pp. 1–22.
Chen et al. (1975) "Evidence for Hemiacetal Formation", *Biochemistry*, vol. 18, No. 5, pp. 921–925.
Davis et al. (1983) "Leucinal Inhibits . . . ", *Pharmacology Biochemistry Behaviour*, vol. 19, pp. 791–794.
Dose, K. (1974) *Origins of Life*, vol. 5, pp. 239–252.
Fasman et al. (1964) *Biochemistry*, vol. 3, No. 11, pp. 1665–1674.
Fox, S.W. et al. (1976) *BioSystems*, vol. 8, pp. 40–44.
Fox, S.W. et al., *Molecular Evolution and the Origin of Life*, Maxel Decker, New York (1977).
Fox, S.W. et al. (1968) *Biochim. Biophys. Acta*, vol. 160, pp. 246–249.
Fox, S.W. (1976) *Origins of Life*, vol. 7, pp. 49–68.
Fox, S.W. (1980) *Naturwissenschaften*, vol. 67, pp. 378–383.
Fox, S.W. et al. (1960) *Archives of Biochemistry and Biophysics*, vol. 86, pp. 281–285.
Fox, S.W. et al. (1974) *Origins of Life*, vol. 5, pp. 227–237.
Fox, S.W. (1984) *Origins of Life*, vol. 14, pp. 485–488.
Gol'dovskii, A.M. (1978) *Zhurnal Evolyutsionnoi Biokhimii i Fiziologii*, vol. 14(6), pp. 437–439.
Gurrieri, S. et al. (1973) *Thermochimica Acta*, vol. 7, pp. 231–239.
Harada, K. et al. (1979) *BioSystems*, vol. 11, pp. 47–53.
Harada et al., (1960) *Archives of Biochemistry and Biophysics*, vol. 86, pp. 274–280.
Hare (1970) *Etude Cenetique De La Polycondensation Thermique D'$_x$–Amino Acides*, vol. 45, pp. 330–339.
Heinrich, M.R. et al. (1969) *Archives of Biochemistry and Biophysics*, vol. 130, pp. 441–448.

(List continued on next page.)

Primary Examiner—Thurman K. Page
Assistant Examiner—William E. Benston, Jr.
Attorney, Agent, or Firm—Darby & Darby

[57] ABSTRACT

Modified amino acid compounds useful in the delivery of active agents are provided. Methods of administration and preparation are provided as well.

27 Claims, No Drawings

U.S. PATENT DOCUMENTS

| | | | |
|---|---|---|---|
| 3,933,873 | 1/1976 | Love et al. | 260/404 |
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 3,976,773 | 8/1976 | Curran | 424/250 |
| 4,035,507 | 7/1977 | Bodor et al. | 424/311 |
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,239,635 | 12/1980 | Rieder | 252/34 |
| 4,239,754 | 12/1980 | Sache et al. | 514/56 |
| 4,272,506 | 6/1981 | Schwarzberg | 424/8 |
| 4,289,759 | 9/1981 | Heavner et al. | 424/177 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,393,192 | 7/1983 | Curatolo et al. | 528/292 |
| 4,402,856 | 9/1983 | Schnoring et al. | 428/402.2 |
| 4,402,968 | 9/1983 | Martin | 424/273 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,460,563 | 7/1984 | Calanchi | 424/35 |
| 4,462,839 | 7/1984 | McGinley et al | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,690,786 | 9/1987 | Ninomiya et al. | 264/4.6 |
| 4,692,284 | 9/1987 | Braden | 264/4.3 |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,886,663 | 12/1989 | Houghten | 424/88 |
| 4,897,444 | 1/1990 | Brynes et al. | 525/54.1 |
| 4,900,730 | 2/1990 | Miyauchi | 514/12 |
| 4,908,233 | 3/1990 | Takizawa et al. | |
| 4,919,939 | 4/1990 | Baker | 424/493 |
| 4,925,673 | 5/1990 | Steiner et al. | 424/455 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,019,400 | 5/1991 | Gombotz et al. | 424/497 |
| 5,023,374 | 6/1991 | Simon | 564/152 |
| 5,039,481 | 8/1991 | Pacifici et al. | 422/4 |
| 5,041,291 | 8/1991 | Bader et al. | 424/426 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,934 | 12/1993 | Goldberg et al. | 424/401 |
| 5,271,961 | 12/1993 | Mathiowitz et al. | 427/213.31 |
| 5,278,148 | 1/1994 | Branca et al. | 514/19 |
| 5,310,535 | 5/1994 | Kruper, Jr. et al. | 424/1.53 |
| 5,328,992 | 7/1994 | Peter et al. | 534/116 |
| 5,352,461 | 10/1994 | Feldstein et al. | 424/493 |
| 5,384,133 | 1/1995 | Boyes et al. | 424/501 |
| 5,389,377 | 2/1995 | Chagnon et al. | 424/450 |
| 5,389,379 | 2/1995 | Dirix et al. | 424/451 |
| 5,401,516 | 3/1995 | Milstein et al. | 424/491 |
| 5,418,010 | 5/1995 | Janda et al. | 427/213.31 |
| 5,443,841 | 8/1995 | Milstein et al. | 424/451 |
| 5,447,728 | 9/1995 | Milstein et al. | 424/490 |
| 5,451,410 | 9/1995 | Milstein et al. | 424/490 |
| 5,536,813 | 7/1996 | Charpenel et al. | |
| 5,540,939 | 7/1996 | Milstein et al. | 424/491 |
| 5,541,155 | 7/1996 | Leone-Bay et al. | 514/2 |
| 5,578,323 | 11/1996 | Milstein et al. | 424/499 |
| 5,601,846 | 2/1997 | Milstein et al. | 424/499 |
| 5,705,529 | 1/1998 | Matyus et al. | 514/541 |

FOREIGN PATENT DOCUMENTS

| | | | |
|---|---|---|---|
| 2 326 934 | 5/1977 | France | A61K 47/00 |
| 2 565 102 | 12/1985 | France | A61K 9/52 |
| 2 424 169 | 12/1974 | Germany | A61K 9/00 |
| 2343037 | 3/1975 | Germany . | |
| 3 202 255 | 10/1982 | Germany | C08L 89/00 |
| 3 612 102.9 | 10/1986 | Germany | C07K 15/00 |
| 71258/2 | 12/1987 | Israel . | |
| 48-24246 | 3/1973 | Japan . | |
| 56-68612 | 6/1981 | Japan | A61K 31/19 |
| 58-35111 | 3/1983 | Japan | A61K 9/66 |
| 6-107682 | 4/1994 | Japan . | |
| 280825 | 12/1964 | Netherlands . | |
| 280826 | 12/1964 | Netherlands . | |
| B-146698 | 11/1982 | Norway | A61K 37/26 |
| 929401 | 6/1963 | United Kingdom . | |
| 1 075 952 | 8/1967 | United Kingdom . | |
| 1 236 885 | 6/1971 | United Kingdom . | |
| 1 567 763 | 5/1980 | United Kingdom | A61K 9/22 |
| 2 095 994 | 10/1982 | United Kingdom | A61K 9/00 |
| WO 85/00105 | 1/1985 | WIPO | A61K 9/52 |
| WO 85/00110 | 1/1985 | WIPO | A61K 47/00 |
| WO 87/04076 | 7/1987 | WIPO | A61K 45/02 |
| WO 88/01213 | 2/1988 | WIPO | B23B 5/16 |
| WO 92/19263 | 12/1992 | WIPO | A61K 39/00 |
| 93/18754 | 9/1993 | WIPO | A61K 9/16 |
| WO 93/25583 | 12/1993 | WIPO | C07K 15/00 |
| WO 94/11015 | 5/1994 | WIPO | A61K 37/00 |
| WO 94/14420 | 7/1994 | WIPO | A61K 9/16 |
| WO 94/18950 | 9/1994 | WIPO | A61K 9/127 |
| WO 94/18997 | 9/1994 | WIPO | A61K 37/00 |

| | | | |
|---|---|---|---|
| WO 94/21234 | 9/1994 | WIPO | A61K 7/00 |
| WO 94/23702 | 10/1994 | WIPO | A61K 9/16 |
| WO 94/23767 | 10/1994 | WIPO | A61L 9/16 |
| WO 94/24291 | 10/1994 | WIPO | A61K 39/05 |
| WO 94/28878 | 12/1994 | WIPO | A61K 9/14 |
| WO 95/11690 | 5/1995 | WIPO | A61K 37/00 |
| WO 85/02772 | 7/1995 | WIPO | A61K 49/00 |
| WO 95/28838 | 11/1995 | WIPO | A01N 37/46 |
| WO 95/28920 | 11/1995 | WIPO | A61K 31/19 |
| WO 96/12473 | 5/1996 | WIPO | A61K 9/16 |
| WO 96/12474 | 5/1996 | WIPO | A61K 9/16 |
| WO 96/12475 | 5/1996 | WIPO | A61K 9/16 |
| WO 96/21464 | 7/1996 | WIPO | A61K 39/00 |
| WO 96/30036 | 10/1996 | WIPO | |
| WO 96/33699 | 10/1996 | WIPO | A61K 9/16 |
| WO 96/39835 | 12/1996 | WIPO | A01N 43/50 |
| WO 96/40070 | 12/1996 | WIPO | A61K 9/14 |
| WO 96/40076 | 12/1996 | WIPO | A61K 9/16 |

OTHER PUBLICATIONS

Heinz, B. et al. (1981) *BioSystems*, vol. 14, pp. 33–40.
Hennon, G. et al. (1975) *Biochimie*, vol. 57, pp. 1395–1396.
Hsu, L.L. et al. (1976) *BioSystems*, vol. 8, pp. 89–101.
Hsu, L.L. et al. (1971) *Currents in Modern Biology*, vol. 4, pp. 12–25.
Ishima, Y. et al. (1981), *BioSystems*, vol. 14, pp. 243–251.
Jackson et al. (1991) "Pharmacological . . . ", *J. Pharm. & Exp. Thera.*, vol. 261, No. 1, pp. 546–552.
Jungck, J.R. et al. (1973) *Naturwissenschaften*, vol. 60, pp. 425–427.
Kokufuta, E. et al. (1984) *BioSystems*, vol. 16, pp. 175–181.
Krampitz, G. et al. (1967) *Naturwissenschaften*, pp. 516–517.
Krampitz, G. et al. (1968) *Naturwissenschaften*, pp. 345–346.
Krampitz, G. et al. (1966) *Naturwissenschaften*, pp. 7 and 8.
Lacey, Jr., J.C. et al. (1979) *BioSystems*, vol. 11, pp. 9–17.
Lacey, Jr., J.C. et al. (1979) *BioSystems*, vol. 11, pp. 1–7.
Martinez Luque–Romero, M. et al. (1986) *BioSystems*, vol. 19, pp. 267–272.
Masinovsky, Z. et al. (1989) *BioSystems*, vol. 22, pp. 305–310.
Matsuno, K. (1982) *BioSystems*, vol. 15, pp. 1–11.
Matsuno, K. (1984) *BioSystems*, vol. 17, pp. 11–14.
Matsuno, K. (1981) *BioSystems*, vol. 14, pp. 163–170.
McAlhaney, W.W. et al. (1976) *BioSystems*, vol. 8, pp. 45–50.
Melius, P. et al. (1987) *BioSystems*, vol. 20, pp. 213–217.
Melius, P. et al. (1975) *Bioorganic Chemistry*, vol. 4, pp. 385–391.
Melius, P. (1979) *BioSystems*, vol. 11, pp. 125–132.
Miquel, J. et al. (1971) *Currents in Modern Biology*, vol. 3, pp. 299–306.
Nakashima, T. et al. (1980) *J. Mol. Evol.*, vol. 15, pp. 161–168.
Nakashima, T. et al. (1981) *BioSystems*, vol. 14, pp. 151–161.
Novak, V.J.A. (1984) *Origins of Life*, vol. 14, pp. 513–522.
Olafsson, P.G. et al. (1971) *Polymer Letters*, vol. 9, pp. 521–528.
Phillips, R.D. et al. (1974) *Int. J. Peptide Protein Res.*, vol. 6, pp. 309–319.
Przybylski, A.T. et al. (1982) *Die Naturwissenschaften*, vol. 69, pp. 561–563.
Przybylski, A.T. et al. (1984) *Applied Biochemistry and Biotechnology*, vol. 10, pp. 301–307.
Przybylski, A.T. (1985) *BioSystems*, vol. 17, pp. 281–288.
Rohlfing, D.L. (1975) *Origins of Life*, vol. 6, pp. 203–209.
Rohlfing, D.L. (1970) *Science*, vol. 169, pp. 998–1000.
Rohlfing, D.L. (1967) *Archives of Biochemistry and Biophysics*, vol. 118, pp. 468–474.
Rohlfing, D.L. et al. *Catalytic Activities of Thermal Polyanhydro–α–Amino Acids*, pp. 373–418.
Rohlfing, D.L. et al. (1976) *BioSystems*, vol. 8, pp. 139–145.
Ryan, J.W. et al. (1973) *BioSystems*, vol. 5, pp. 115–118.
Saunders, M.A. et al. (1974) *BioSystems*, vol. 6, pp. 81–92.
Snyder, W.D. et al. (1975) *BioSystems*, vol. 7, pp. 222–229.
Sokol, P.E. (1974) *Journal of the American Oil Chemists'Society*, vol. 52, pp. 101–102.
Tschager et al. (1988) *Milchwirtschaftliche Berichte*, vol. 95, pp. 79–83.
Vaughan, G. et al. (1987) *BioSystems*, vol. 20, pp. 219–223.
Vol'kenshtein, M.V. (1989) *Molekulyarnaya Biologiya*, vol. 23(1), pp. 23–37.
Waehneldt, T.V. et al. (1968) *Biochim. Biophys. Acta*, vol. 160, pp. 239–245.
Williams et al. (1991) *J. Biol. Chem.*, vol. 266, No. 8, pp. 5182–5190.
Yuki, A. et al. (1969) *Biochemical and Biophysical Research Communications*, vol. 36(4), pp. 657–663.
Zulaski et al. (1983) "New Carboxyalkyl Inhibitors of Brain Enkenphalinase", *J. Med. Chem.*, 26, pp. 60–65.
(1985) *Chemical Abstracts*, vol. No. 105(1), Abstract No. 12027p.
(1985) *Chemical Abstracts*, vol. No. 102(6), Abstract No. 50870d.
*Chemical Abstract*, vol. 80(9) Abst. No. 52392a.
Bergeron, Raymond J., et al. (1994) "Macromolecular Self–Assembly of Diketopiperazine Tetrapeptides", *Journal of the American Chemical Society*, vol. 116, pp. 8479–8484.
Bergeron, Raymond J., et al. (1993) "A Comparative Study of the Iron–Clearing Properties of Desferrithiocin Analogues With Desferrioxamine B in a Cebus Monkey Model", *Blood*, vol. 81, No. 8, pp. 2166–2173.
Bergeron, Raymond J., et al., (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood*, vol. 79, No. 7, pp. 1882–1890.
Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.
Bergeron, Raymond et al., "A Comparative Evaluation of Iron Clearance Models", *Annals New York Academy of Sciences*, pp. 278–393.
Andriuoli, G., et al. (1990), *Haemostasis* 20 (suppl. 1):154–158.
Caramazza, I., et al. (1991), *Thrombosis Research* 62:785–789.
Guarini, S., et al. (1983), *Experimentia* 41:350–352.
Guarini, S., et al. (1985), *Pharmacological Research Communications* 17(8):685–697.
Dal Pozzo, A., et al. (1989), *Thrombosis Research* 56:119–124.
Gelb, R., et al (1983), *Lite Sciences* 33(1):83–85.
Watterberg et al. (1988), *Pediatric Research*, vol. 23, No. 4, part 2, p. 570A, col. 1, abstract No. 2209.
Bernstein (1985), *Chest* 87(1):68S–73S.
Damge et al. (1988), *Diabetes* 37:246–251.
*Chemical Abstracts*:83 184360k, (1975).
Amino, Y., et al., *Chem. Pharm. Bull.* 36(11):4426–4434 (1988).
Baughman, R.A. et al., *Proc. of the 6th Inter'l. Symp. on Recent Advs. in Drug Delivery Systems, Ctr. for Controlled Chem. Delivery, University of Utah*, Feb. 22–25, 1993, Salt Lake City, UT, pp. 179–180 "Method for Assessing The Stability of Proteinoid Microspheres".

Haas, S. et al., "Assessment Of Stability Of Proteinoid Microspheres", *Proceed. Intern. Symp. Control. Rel. Biact. Mater.*, 20 (1993), Controlled Release Society, Inc.,.

X. Ma, et al., *Proceed. Intern. Symp. Control. Rel. Bioact. Mater.*, 20 (1993), Controlled Release Society, Inc. "In Vitro Mechanistic Investigation of the Proteinoid Microsphere Oral Delivery System".

Yen, H.–R H., et al., "Adsorption of Sulforhodamine 101 on Proteinoid Microspheres" *Proceed. Intern. Symp. Control. Rel. Bioact. Mater.*, 20 (1993), Controlled Release Society, Inc.

Presented at *"IBC Rational Drug Design Conference"*, San Diego, Calif.—Dec. 1994.

Leone–Bay et al., Presented at *"Winter Conference on Medicinal and Bioorganic Chemistry"* Steamboat Springs, Colorado—Feb. 1995 "Microsphere Formation and Drug Delivery in a Series of Derivatized Amino Acids".

Santiago et al., *Pharm. Res.* 11:1994, p. S–298 "Oral Delivery of Heparin Microspheres made with Modified Amino Acids".

Leone–Bay et al., *Pharm. Res.* 11: 1994, p. S–121 "Oral Delivery of Heparin using Acylated Amino Acids".

Sarubbi et al., *Pharm. Res.* 11: 1994, p. S–299 "Oral Calcitonin Delivery using the PODDS Technology".

Leipold et al., *Pharm. Res.* 11: 1994, p. S–298 "Oral Delivery of Interferon in Rats and Primates".

Santiago et al., *Pharm. Res.* 11: 1994, p. S–298 "Evaluation in Rats of Vehicles for the Oral Delivery of Low Molecular Weight Heparin".

X. Ma et al., PDD 7303 *Pharmaceutical Research* 9(10):S–244, 1992 (Oct. Supplement).

Milstein et al., *Symposia Abstracts*. AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater.*, 20 (1993), Controlled Release Society, Inc.

Santiago et al. "Oral Immunization of Rats with Influenza Virus M Protein (M1) Microspheres" *Proceed. Intern. Symp. Control. Rel. Bioact. Mater.*, 19 (1992), Controlled Release Society, Inc., pp. 116–117.

Santiago et al. "Proteinoid Microspheres For The Oral Delivery of Heparin" *Proceed. Intern. Symp. Control. Rel. Bioact. Mater.*, 19 (1992), Controlled Release Society, Inc. pp. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater.*, 19 (1992), Controlled Release Society, Inc. pp. 516–517.

Doris K. Chiappetta, *Eastern Analytical Symposium*, Nov. 17, 1992 "Solutions for Problems in Bioanalysis".

Elizabeth A. Harris. M.S., *Eastern Analytical Symposium*, Nov. 17, 1992 "Solutions for Problems in Bioanalysis".

*AAPS 6th Ann. Meeting and Expo.*, "Proteinoids—A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond*, Jan. 17–22, 1993.

Xinghang Ma, et al. "Stability Study of Drug–loaded Proteinoid Microsphere Formulations during Freeze–drying" *Journal of Drug Targeting*, 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems*, Ctr. for Controlled Chem. Delivery, University of Utah, Feb. 22–25, 1993, pp. 181–182.

Robert O. Dillman, M.D., *Annals of Internal Medicine* 1989:111 pp. 592–600, "Monoclonal Antibodies for Treating Cancer".

Brendan D. Curti, *Critical Reviews in Oncology/Hematology*, 1993: 14 pp. 29–39 "Physical barriers to drug delivery in tumors".

V. Hird et al, *Genes and Cancer*, edited by Desmond Carney & Karol Sikora, pp. 183–189, Immunotherapy with Monoclonal Antibodies.

Michael E. Osband et al., *Immunology Today*, vol. 11, No.6 1990, pp. 93–95, "Problems in the investigational study and clinical use of cancer immunotherapy".

William J. Harris, *Tibtech* Feb. 1993 vol. 11, pp. 42–44 "Therapeutic antibodies—the coming of age".

Thomas A. Waldmann, *Science*, Jun. 21, 1991, 252:1657–1662, "Monoclonal Antibodies in Diagnosis and Therapy".

*Chemical Abstracts*, 76(14):72994u, (1971).

*Chemical Abstracts*, 84(7):44660d, (1975).

*Chemical Abstracts*, 86(16):107529g, (1976).

*Chemical Abstracts*, 112(15):134663h, (1989).

*Chemical Abstracts*, 114(22):214519x, (1990).

J. Györe et al., *Thermal Analysis*, vol. 2—Proceeding Fourth ICTA Budapest 1974, pp. 387–394.

*Chemical Abstracts*, 99(19) 158832b, (1982).

*Derwent Abstracts*, JP 67008622, (1967).

*Journal of Medicinal Chemistry*, vol. 38, No. 21, pp. 4257–4262, (1995), "Microsphere Formation in a Series of Derivatized α–Amino Acids: Properties, Molecular Modeling, and Oral Delivery of Salmon Calcitonin".

Andrea Leone–Bay et al., *Journal of Medicinal Chemistry*, vol. 38, No. 21, pp. 4263–4269, (1995), "N–Acylated α–Amino Acids as Novel Oral Delivery Agents for Proteins".

*The Extra Pharmacopoeia*, Thirtieth Edition, pp. 325–326, (1993).

Stephen J. Douglas et al., *Chemistry and Industry*, vol. 22:748–751, 1985.

C.A. Finch, *Chemistry and Industry*, vol. 22:752–756, 1985.

John A. Butera et al., *J. Med. Chem.*, vol. 34:3212–3228, 1990.

Madeline G. Cimini et al., *Ann. Report in Med Chem.*, vol. 27:89–98., 1992.

Bernadette Earley et al., *Brain Research*, vol. 546:282–286, 1991.

John W. Ellingboe et al., *J. Med Chem.*, vol. 35:705–716, 1992.

William C. Lumma et al., *J. Med Chem.*, vol. 30:758–763, 1987.

Joseph J. Lynch et al., *J. of Pharm. and Exp. Therap.*, vol. 269:541–554, 1994.

Kiyoshi Matsuno et al., *Brain Research*, vol. 575:315–319, 1992.

Thomas K. Morgan et al., *J. Med. Chem.*, vol. 33:1091–1097, 1990.

Hitoshi Oinuma et al., *J. Med Chem.*, vol. 33:903–905, 1990.

Tadimeti S. Rao et al., *Molecular Pharmacology*, vol.37:978–982, 1990.

COMPOUNDS AND COMPOSITIONS FOR DELIVERING ACTIVE AGENTS

This is a division of application Ser. No. 08/335,148, filed Oct. 25, 1994 now U.S. Pat. No. 5,613,957, which in turn is (a) a continuation-in-part of PCT/US94/04560, filed Apr. 22, 1994; which is a continuation-in-part of Ser. No. 08/051,019, filed Apr. 22, 1993; now U.S. Pat. No. 5,451,410 and of Ser. No. 08/205,511, filed Mar. 2, 1994; allowed Sep. 30, 1997, and (b) a continuation-in-part of Ser. No. 08/231,622, filed Apr. 22, 1994 now U.S. Pat. No. 5,629,020.

FIELD OF THE INVENTION

The present invention relates to compounds for delivering active agents, and particularly biologically active agents such as, for example, bioactive peptides and the like. These compounds are used as carriers to facilitate the delivery of a cargo to a target. The carriers are modified amino acids and are well suited to form non-covalent mixtures with biologically-active agents for oral administration to animals. Methods for the preparation and for the administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself.

Biologically active agents are particularly vulnerable to such barriers. For example in the delivery to animals of pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of oral delivery systems. Oral delivery of many biologically active agents would be the route of choice for administration to animals if not for biological, chemical, and physical barriers such as varying pH in the gastro-intestinal (GI) tract, powerful digestive enzymes, and active agent impermeable gastro-intestinal membranes. Among the numerous agents which are not typically amenable to oral administration are biologically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastro-intestinal tract by acid hydrolysis, enzymes, or the like.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), *FEBS Letters*, Vol. 62, pg. 60; and Hashimoto et al. (1979), *Endocrinology Japan*, Vol. 26, pg. 337.

However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

There is still a need in the art for simple, inexpensive delivery systems which are easily prepared and which can deliver a broad range of active agents.

SUMMARY OF THE INVENTION

Compounds useful in the delivery of active agents are provided. These compounds include

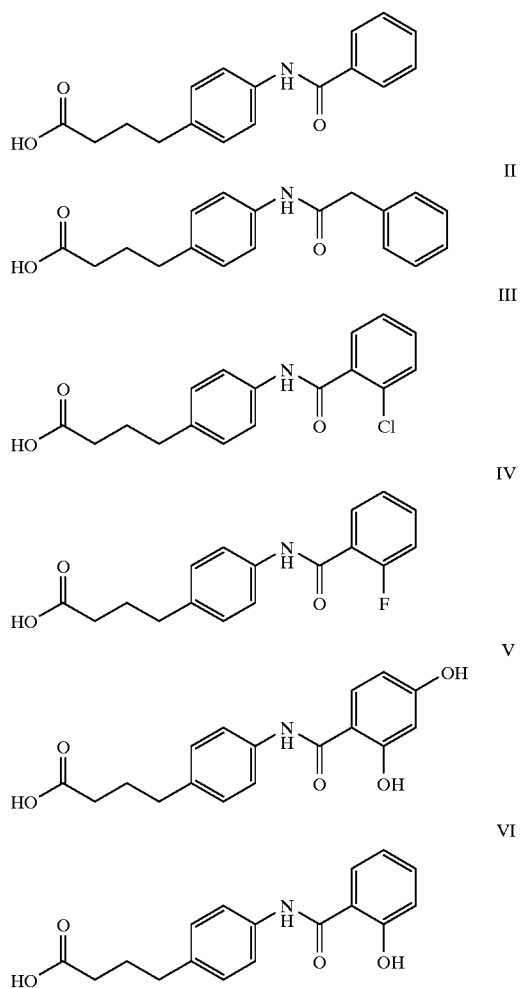

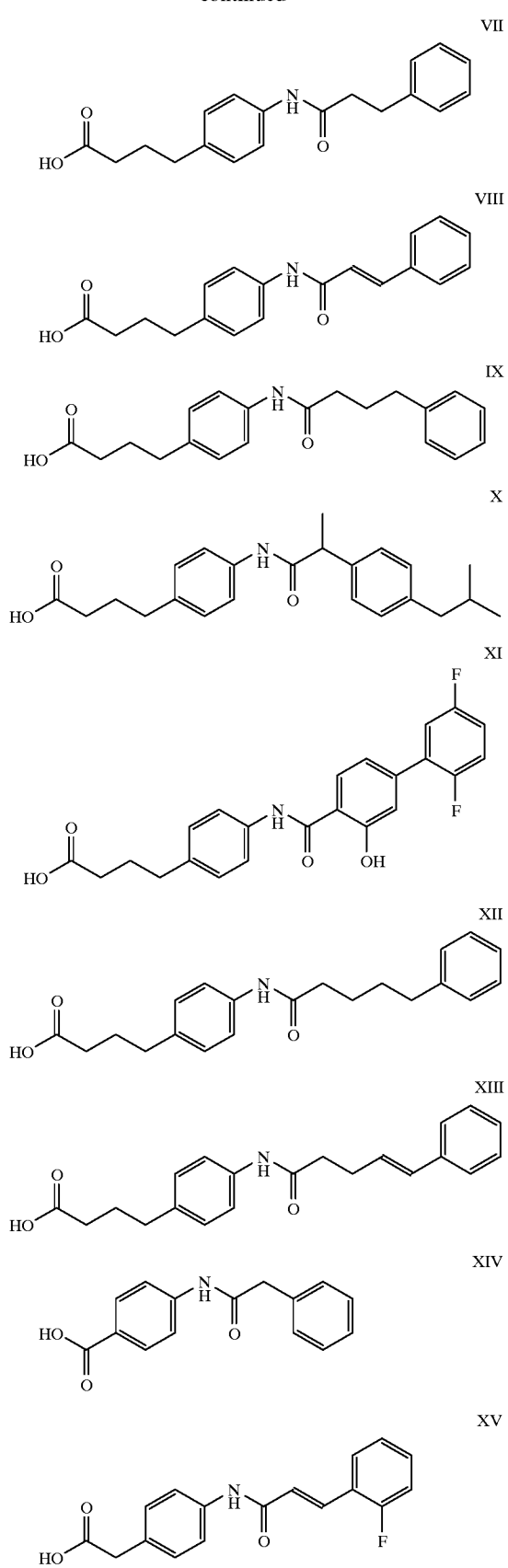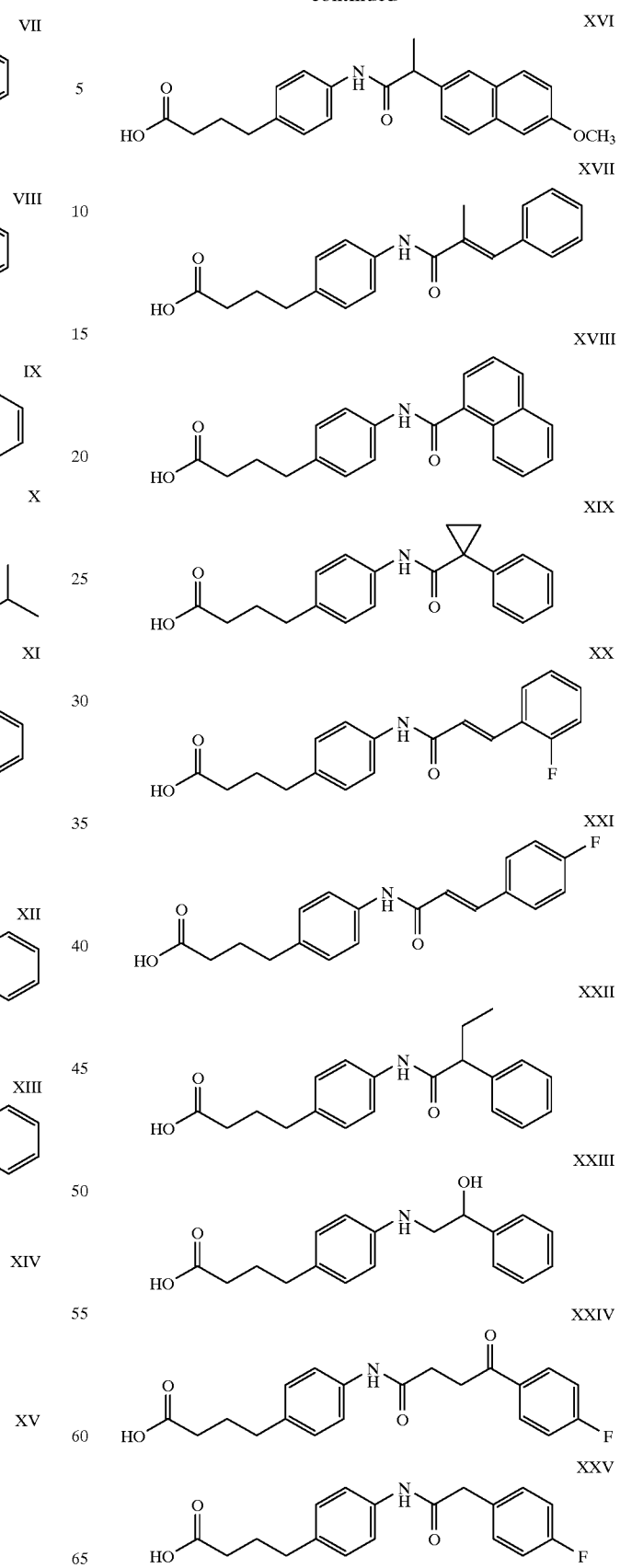

XXVI
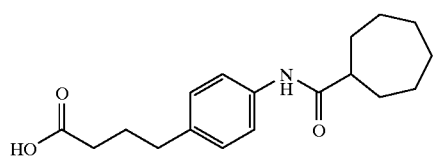
XXVII
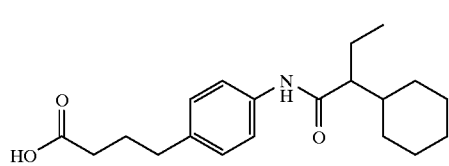
XXVIII
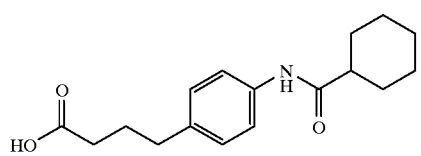
XXIX
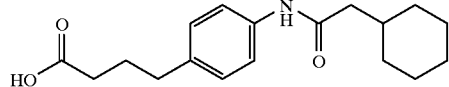
XXX
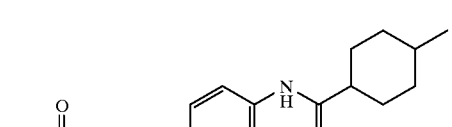
XXXI
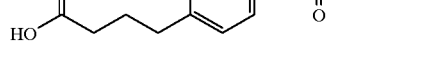
XXXII
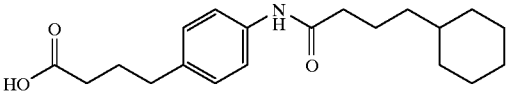
XXXIII
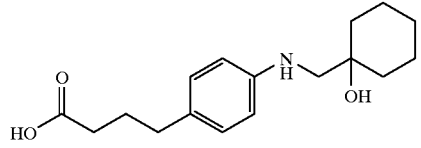
XXIV
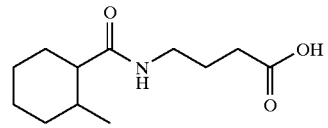
XXXV
XXXVI
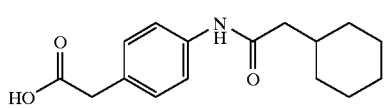
XXXVII
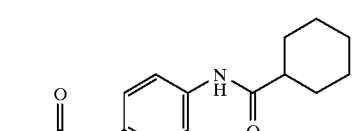
XXXVIII
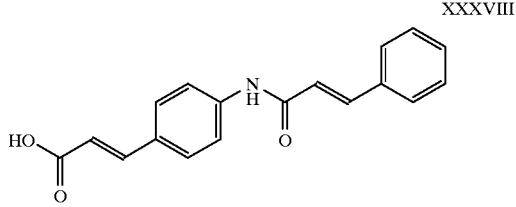
XXXIX
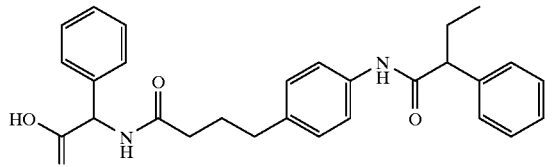
XL
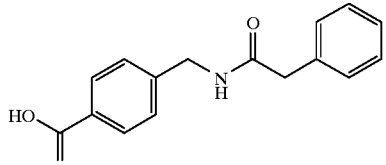
XLI
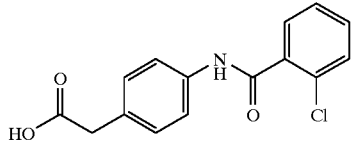
XLII
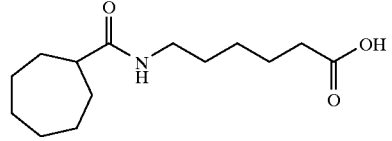
XLIII
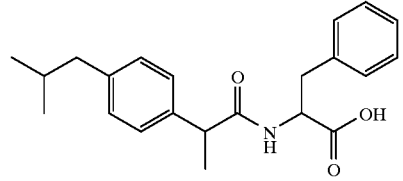

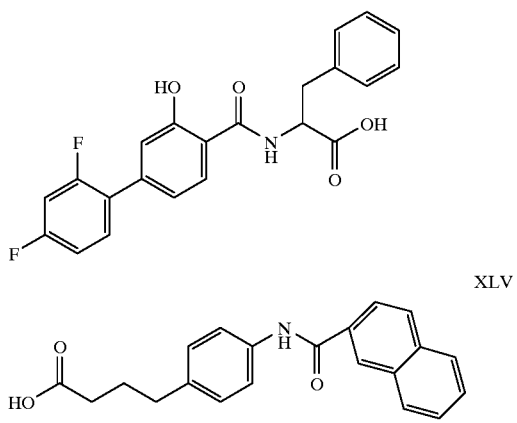

XLIV

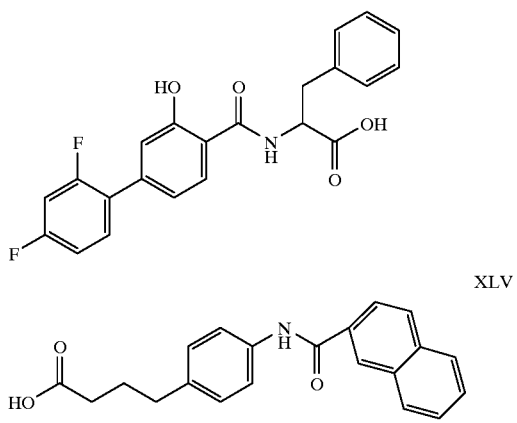

XLV or salts thereof.

Compositions comprising at least one biologically active agent and at least one of the compounds above are also provided. Further contemplated by the present invention are dosage unit forms that include these compositions.

Also contemplated is a method for preparing these compositions which comprises mixing at least one active agent with at least one compound as described above, and optionally, a dosing vehicle.

In an alternative embodiment, these non-toxic compounds are orally administered to animals as part of a delivery system by blending or mixing the compounds with an active agent prior to administration.

DETAILED DESCRIPTION OF THE INVENTION

The specific compounds of the present invention or salts thereof such as, for example, sodium salts, may be used to deliver various active agents through various biological, chemical, and physical barriers. These compounds are particularly suited for delivering active agents which are subject to environmental degradation. The compounds and compositions of the subject invention are particularly useful for delivering or administering biologically-active agents to any animals such as birds; mammals, such as primates and particularly humans; and insects.

Other advantages of the present invention include the use of easy to prepare, inexpensive raw materials. The compositions and the formulation methods of the present invention are cost effective, simple to perform, and amenable to industrial scale up for commercial production.

Amino acids, poly amino acids, and peptides, in modified form, may be used to deliver active agents including, but not limited to, biologically active agents such as for example, pharmacological and therapeutic agents.

An amino acid is any carboxylic acid having at least one free amine group and includes naturally occurring and synthetic amino acids.

Poly amino acids are either peptides or two or more amino acids linked by a bond formed by other groups which can be linked, e.g. an ester, anhydride, or an anhydride linkage. Special mention is made of non-naturally occurring poly amino acids and particularly non-naturally occurring hetero poly amino acids, i.e. polymers of mixed amino acids.

Peptides are two or more amino acids joined by a peptide bond. Peptides can vary in length from dipeptides with two amino acids to poly peptides with several hundred amino acids. See *Chambers Biological Dictionary*, editor Peter M. B. Walker, Cambridge, England: Chambers Cambridge, 1989, page 215. Special mention is made of di-peptides, tri-peptides, tetra-peptides, and penta-peptides.

The terms modified amino acids, modified poly amino acids, and modified peptides are meant to include amino acids which have been modified or poly amino acids and peptides in which at least one amino acid has been modified by acylating at least one free amine group with an acylating agent which reacts with at least one of the free amine groups present.

Modified Amino Acids

Several of the compounds of the present invention are broadly represented by one of formula XLVI or XLVII below:

   XLVI wherein Ar is a substituted or unsubstituted phenyl or naphthyl;

Y is

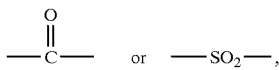

$R^1$ has the formula

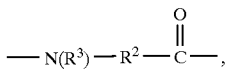

wherein:
$R^2$ is $C_1$ to $C_{24}$ alkyl, $C_1$ to $C_{24}$ alkenyl, phenyl, naphthyl, ($C_1$ to $C_{10}$ alkyl) phenyl, ($C_1$ to $C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl), and naphthyl ($C_1$ to $C_{10}$ alkenyl);

$R^2$ is optionally substituted with $C_1$ to $C_4$ alkyl, $C_1$ to $C_4$ alkenyl, $C_1$ to $C_4$ alkoxy, —OH, —SH and —$CO_2R^4$ or any combination thereof;

$R^4$ is hydrogen, $C_1$ to $C_4$ alkyl or $C_1$ to $C_4$ alkenyl;

$R^2$ is optionally interrupted by oxygen, nitrogen, sulfur or any combination thereof; and $R^3$ is hydrogen, $C_1$ to $C_4$ alkyl or $C_1$ to $C_4$ alkenyl; or

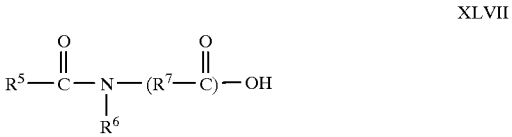   XLVII wherein:
$R^5$ is (i) $C_3$–$C_{10}$ cycloalkyl, optionally substituted with $C_1$–$C_7$ alkyl, $C_2$–$C_7$ alkenyl, $C_1$–$C_7$ alkoxy, hydroxy, phenyl, phenoxy or —$CO_2R^8$, wherein
$R^8$ is hydrogen, $C_1$–$C_4$ alkyl, or $C_2$–$C_4$ alkenyl; or
(ii) $C_1$–$C_6$ alkyl substituted with $C_3$–$C_{10}$ cycloalkyl;

$R^6$ is hydrogen, $C_1$–$C_4$ alkyl, or $C_2$–$C_4$ alkenyl;

$R^7$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl) or naphthyl ($C_2$–$C_{10}$ alkenyl);

$R^7$ being optionally substituted with $C_1$–$C_4$ alkyl, $C_2$–$C_4$ alkenyl, $C_1$–$C_4$ alkoxy, —OH, —SH, —$CO_2R^9$, $C_3$–$C_{10}$ cycloalkyl, $C_3$–$C_{10}$ cycloalkenyl, heterocycle having 3–10 ring atoms wherein the hetero atom is one or more of N, O, S or any combination thereof, aryl, ($C_1$–$C_{10}$ alkaryl, ar($C_1$–$C_{10}$ alkyl), or any combination thereof;

$R^7$ being optionally interrupted by oxygen, nitrogen, sulfur, or any combination thereof; and $R^9$ is hydrogen, $C_1$–$C_4$ alkyl, or $C_2$–$C_4$ alkenyl.

Special mention is made of compounds I–XLV above.

The modified amino acids of compounds I–XLV may be prepared by reacting single amino acids, mixtures of two or more amino acids, amino acid esters, or amino acid amides, with an amine modifying agent which reacts with free amino moieties present in the amino acids to form amides.

Modified amino acids are typically prepared by modifying the amino acids or an ester thereof. Many of these compounds are prepared by acylation with acylating agents having the formula

XLVIII

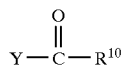

wherein: $R^{10}$ is the appropriate radical to yield the modification indicated in the final product as would be within the skill of the art based upon the detailed disclosure herein, and Y is a leaving group. Typical leaving groups include, but are not limited to, halogens such as, for example, chlorine, bromine, and iodine. Additionally, the corresponding anhydrides are suitable acylating agents.

Many of the compounds of the present invention can be readily prepared and modified by methods within the skill of those in the art based upon the present disclosure. For example, the modified amino acid compounds above may be prepared by reacting the single amino acid with the appropriate acylating agent or an amine modifying agent which reacts with free amino moiety present in the amino acids to form amides. Protecting groups may be used to avoid unwanted side reactions as would be known to those skilled in the art.

For example, the amino acid can be dissolved in aqueous alkaline solution of a metal hydroxide, e.g., sodium or potassium hydroxide, and heated at a temperature ranging between about 5° C. and about 70° C., preferably between about 10° C. and about 40° C., for a period ranging between about 1 hour and about 4 hours, preferably about 2.5 hours. The amount of alkali employed per equivalent of $NH_2$ groups in the amino acid generally ranges between about 1.25 and about 3 mmole, preferably between about 1.5 and about 2.25 mmole per equivalent of $NH_2$. The pH of the solution generally ranges between about 8 and about 13, preferably ranging between about 10 and about 12.

Thereafter, the appropriate amino modifying agent is added to the amino acid solution while stirring. The temperature of the mixture is maintained at a temperature generally ranging between about 5° C. and about 70° C., preferably between about 10° C. and about 40° C., for a period ranging between about 1 and about 4 hours. The amount of amino modifying agent employed in relation to the quantity of amino acid is based on the moles of total free $NH_2$ in the amino acid. In general, the amino modifying agent is employed in an amount ranging between about 0.5 and about 2.5 mole equivalents, preferably between about 0.75 and about 1.25 equivalents, per molar equivalent of total $NH_2$ group in the amino acid.

The reaction is quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded, and the modified amino acid is collected from the lower layer by filtration or decantation. The crude modified amino acid is then dissolved in water at a pH ranging between about 9 and about 13, preferably between about 11 and about 13. Insoluble materials are removed by filtration and the filtrate is dried in vacuo. The yield of modified amino acid generally ranges between about 30 and about 60%, and usually about 45%.

If desired, amino acid esters, such as, for example methyl or ethyl esters of amino acid compounds, may be used to prepare the modified amino acids of the invention. The amino acid ester, dissolved in a suitable organic solvent such as dimethylformamide or pyridine, is reacted with the appropriate amino modifying agent at a temperature ranging between about 5° C. and about 70° C., preferably about 25° C., for a period ranging between about 7 and about 24 hours. The amount of amino modifying agent used relative to the amino acid ester is the same as described above for amino acids.

Thereafter, the reaction solvent is removed under negative pressure and the ester functionality is removed by hydrolyzing the modified amino acid ester with a suitable alkaline solution, e.g. 1 N sodium hydroxide, at a temperature ranging between about 50° C. and about 80° C., preferably about 70° C., for a period of time sufficient to hydrolyze off the ester group and form the modified amino acid having a free carboxyl group. The hydrolysis mixture is then cooled to room temperature and acidified, e.g. aqueous 25% hydrochloric acid solution, to a pH ranging between about 2 and about 2.5. The modified amino acid precipitates out of solution and is recovered by conventional means such as filtration or decantation.

The modified amino acid may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, preferably a subsequent 0–500 mM sodium chloride gradient is employed.

Active Agents

Active agents suitable for use in the present invention include biologically active agents, chemically active agents, including, but not limited to, fragrances, as well as other active agents such as, for example, cosmetics.

Biologically active agents include, but are not limited to, pesticides, pharmacological agents, and therapeutic agents. For example, biologically active agents suitable for use in the present invention include, but are not limited to, peptides, and particularly small peptides; hormones, and particularly hormones which by themselves do not or only pass slowly through the gastro-intestinal mucosa and/or are susceptible to chemical cleavage by acids and enzymes in the gastro-intestinal tract; polysaccharides, and particularly mixtures of muco-polysaccharides; carbohydrates; lipids; or any combination thereof. Further examples include, but are not limited to, human growth hormones; bovine growth hormones; growth releasing hormones; interferons; interleukin-1; insulin; heparin, and particularly low molecular weight heparin; calcitonin; erythropoietin; atrial naturetic factor; antigens; monoclonal antibodies; somatostatin; adrenocorticotropin, gonadotropin releasing hormone; oxytocin; vasopressin; cromolyn sodium (sodium or disodium chromoglycate); vancomycin; desferrioxamine (DFO); anti-microbials, including, but not limited to anti-fungal agents; or any combination thereof.

Delivery Systems

The compositions of the present invention may include one or more active agents.

In one embodiment, compounds I–XLV or poly amino acids or peptides that include at least one of these compounds may be used directly as a drug delivery carrier by simply mixing one or more compound, poly amino acid or peptide with the active ingredient prior to administration.

In an alternative embodiment, the compounds, poly amino acids, or peptide may be used to form microspheres containing the active agent. These compounds, poly amino acids, or peptides are particularly useful for the oral administration of certain biologically-active agents, e.g., small peptide hormones, which, by themselves, do not pass or only pass slowly through the gastro-intestinal mucosa and/or are susceptible to chemical cleavage by acids and enzymes in the gastrointestinal tract.

If the modified amino acids, poly amino acids, or peptides are to be converted into microspheres, the mixture is optionally heated to a temperature ranging between about 20 and about 50° C., preferably about 40° C., until the modified amino acid(s) dissolve. The final solution contains between from about 1 mg and to about 2000 mg of compound, poly amino acid, or peptide per mL of solution, preferably between about 1 and about 500 mg per mL. The concentration of active agent in the final solution varies and is dependent on the required dosage for treatment. When necessary, the exact concentration can be determined by, for example, reverse phase HPLC analysis.

When the compounds, poly amino acids, or peptides are used to prepare microspheres, another useful procedure is as follows: Compounds, poly amino acids, or peptides are dissolved in deionized water at a concentration ranging between about 75 and about 200 mg/ml, preferably about 100 mg/ml at a temperature between about 25° C. and about 60° C., preferably about 40° C. Particulate matter remaining in the solution may be removed by conventional means such as filtration.

Thereafter, the compound, poly amino acid, or peptide solution, maintained at a temperature of about 40° C., is mixed 1:1 (V/V) with an aqueous acid solution (also at about 40° C.) having an acid concentration ranging between about 0.05 N and about 2 N, preferably about 1.7 N. The resulting mixture is further incubated at 40° C. for a period of time effective for microsphere formation, as observed by light microscopy. In practicing this invention, the preferred order of addition is to add the compound, poly amino acid, or peptide solution to the aqueous acid solution.

Suitable acids for microsphere formation include any acid which does not
 (a) adversely effect the modified amino acids, poly amino acids, or peptides e.g., initiate or propagate chemical decomposition;
 (b) interfere with microsphere formation;
 (c) interfere with microsphere incorporation of the cargo; and
 (d) adversely interact with the cargo.

Preferred acids for use in this aspect include acetic acid, citric acid, hydrochloric acid, phosphoric acid, malic acid and maleic acid.

A microsphere stabilizing additive may be incorporated into the aqueous acid solution or into the compound or cargo solution prior to the microsphere formation process. With some drugs the presence of such additives promotes the stability and/or dispersibility of the microspheres in solution.

The stabilizing additives may be employed at a concentration ranging between about 0.1 and 5% (w/v), preferably about 0.5% (w/v). Suitable, but non-limiting, examples of microsphere stabilizing additives include gum acacia, gelatin, methyl cellulose, polyethylene glycol, and polylysine. The preferred stabilizing additives are gum acacia, gelatin and methyl cellulose.

Under the above conditions, the compound molecules, poly amino acids, or peptides form hollow or solid matrix type microspheres wherein the cargo is distributed in a carrier matrix or capsule type microspheres encapsulating liquid or solid cargo. If the compound, poly amino acid, or peptide microspheres are formed in the presence of a soluble material, e.g., a pharmaceutical agent in the aforementioned aqueous acid solution, this material will be encapsulated within the microspheres. In this way, one can encapsulate pharmacologically active materials such as peptides, proteins, and polysaccharides as well as charged organic molecules, e.g., antimicrobial agents, which normally have poor bioavailability by the oral route. The amount of pharmaceutical agent which may be incorporated by the microsphere is dependent on a number of factors which include the concentration of agent in the solution, as well as the affinity of the cargo for the carrier. The compound, poly amino acid, or peptide microspheres do not alter the physiological and biological properties of the active agent. Furthermore, the encapsulation process does not alter the pharmacological properties of the active agent. Any pharmacological agent can be incorporated within the microspheres. The system is particularly advantageous for delivering chemical or biological agents which otherwise would be destroyed or rendered less effective by conditions encountered within the body of the animal to which it is administered, before the microsphere reaches its target zone (i.e., the area in which the contents of the microsphere are to be released) and for delivering pharmacological agents which are poorly absorbed in the gastrointestinal tract. The target zones can vary depending upon the drug employed.

The particle size of the microsphere plays an important role in determining release of the active agent in the targeted area of the gastro-intestinal tract. The preferred microspheres have diameters between about ≦0.1 microns and about 10 microns, preferably between about 0.5 microns and about 5 microns. The microspheres are sufficiently small to release effectively the active agent at the targeted area within the gastro-intestinal tract such as, for example, between the stomach and the jejunum. Small microspheres can also be administered parenterally by being suspended in an appropriate carrier fluid (e.g., isotonic saline) and injected directly into the circulatory system, intramuscularly or subcutaneously. The mode of administration selected will vary, of course, depending upon the requirement of the active agent being administered. Large amino acid microspheres (>50 microns) tend to be less effective as oral delivery systems.

The size of the microspheres formed by contacting compounds, poly amino acids, or peptides with water or an aqueous solution containing active agents can be controlled by manipulating a variety of physical or chemical parameters, such as the pH, osmolarity or ionic strength of the encapsulating solution, size of the ions in solution and by the choice of acid used in the encapsulating process.

The administration mixtures are prepared by mixing an aqueous solution of the carrier with an aqueous solution of the active ingredient, just prior to administration. Alternatively, the carrier and the biologically active ingredient can be admixed during the manufacturing process. The solutions may optionally contain additives such as phosphate buffer salts, citric acid, acetic acid, gelatin and gum acacia.

Stabilizing additives may be incorporated into the carrier solution. With some drugs, the presence of such additives promotes the stability and dispersibility of the agent in solution.

The stabilizing additives may be employed at a concentration ranging between about 0.1 and 5% (W/V), preferably about 0.5% (W/V). Suitable, but non-limiting, examples of stabilizing additives include gum acacia, gelatin, methyl cellulose, polyethylene glycol, and polylysine. The preferred stabilizing additives are gum acacia, gelatin and methyl cellulose.

The amount of active agent is an amount effective to accomplish the purpose of the particular active agent. The amount in the composition typically is a pharmacologically or biologically effective amount. However, the amount can be less than a pharmacologically or biologically effective amount when the composition is used in a dosage unit form, such as a capsule, a tablet or a liquid, because the dosage unit form may contain a multiplicity of carrier/biologically active agent compositions or may contain a divided pharmacologically or biologically effective amount. The total effective amounts can then be administered in cumulative units containing, in total, pharmacologically or biologically active amounts of biologically or pharmacologically active agent.

The total amount of active agent, and particularly biologically active agent, to be used can be determined by those skilled in the art. However, it has surprisingly been found that with some biologically active agents, the use of the presently disclosed carriers provides extremely efficient delivery. Therefore, lower amounts of biologically active agent than those used in prior dosage unit forms or delivery systems can be administered to the subject, while still achieving the same blood levels and therapeutic effects.

The amount of carrier in the present composition is a delivery effective amount and can be determined for any particular carrier or biologically active agent by methods known to those skilled in the art.

Dosage unit forms can also include any of excipients; diluents; disintegrants; lubricants; plasticizers; colorants; and dosing vehicles, including, but not limited to water, 1,2-propane diol, ethanol, olive oil, or any combination thereof.

Administration of the present compositions or dosage unit forms preferably is oral or by intraduodenal injection.

The delivery compositions of the present invention may also include one or more enzyme inhibitors. Such enzyme inhibitors include, but are not limited to, compounds such as actinonin or epiactinonin and derivatives thereof. These compounds have the formulas below:

XLIX

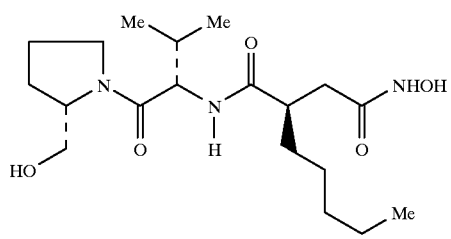

Actinonin

-continued

L

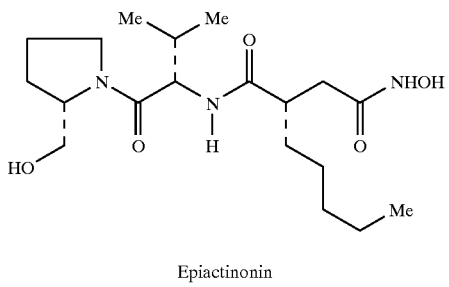

Epiactinonin

Derivatives of these compounds are disclosed in U.S. Pat. No. 5,206,384. Actinonin derivatives have the formula:

LI

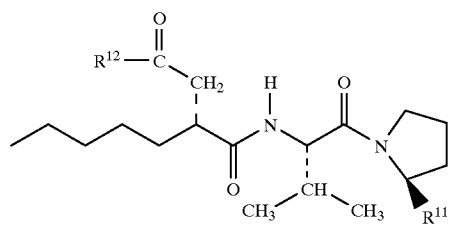

wherein $R^{12}$ is sulfoxymethyl or carboxyl or a substituted carboxy group selected from carboxamide, hydroxyaminocarbonyl and alkoxycarbonyl groups; and $R^{13}$ is hydroxyl, alkoxy, hydroxyamino or sulfoxyamino group. Other enzyme inhibitors include, but are not limited to, aprotinin (Trasylol) and Bowman-Birk inhibitor.

The compounds and compositions of the subject invention are useful for administering biologically active agents to any animals such as birds; mammals, such as primates and particularly humans; and insects. The system is particularly advantageous for delivering chemically or biologically active agents which would otherwise be destroyed or rendered less effective by conditions encountered before the active agent its target zone (i.e. the area in which the active agent of the delivery composition are to be released) and within the body of the animal to which they are administered. Particularly, the compounds and compositions of the present invention are useful in orally administering active agents, especially those which are not ordinarily orally deliverable.

DESCRIPTION OF THE PREFERRED EMBODIMENTS

The following examples illustrate the invention without limitation.

EXAMPLE 1

Compound VI was prepared as follows:
Acetylsalicyloyl chloride (47.00 g, 0.24 mol, 1 equiv.) was added portionwise to a mixture of 4-(4-aminophenyl)butyric acid (50.00 g, 0.28 mol, 1.2 equiv.) in aqueous sodium hydroxide (2 M, 300 mL). The reaction was stirred at 25° C. for 2 hours, and the resultant solution was acidified with aqueous hydrochloric acid (1 M) to pH 2.1. The resultant precipitate was filtered, and was washed with aqueous hydrochloric acid (1 M, 3×100 mL) and water to give Compound VI as a pale pink solid (31.89 g, 52%).

Properties are listed below.

¹H NMR (300 MHz, DMSO-d₆) δ: 7.74 (1H, dd), 7.38 (2H, d), 7.21; (3H, m), 6.67 (1H, m), 6.57 (1H, m), 2.48 (2H, t), 2.07 (2H, t), 1.71 (2H, m). Anal. Calcd for $C_{17}H_{17}NO_4$: C, 68.20; H, 5.73; N, 4.70. Found: C, 68.22; H, 5.61; N, 4.66.

Similar procedures were used to prepare Compounds II, V, X, XIV, XVIII, XXII, XXV, XXVI, XXVII, XXVIII, XXIX, XXX, XXXIII, XXXIV, XXXV, XXXVI, XXXVII, XXXVIII, XL, XLI, XLII, and XLV.

Properties are listed below.

Compound II—¹H NMR (300 MHz, D₂O): δ7.23(9H, m), 3.62(2H, s), 2.50(2H, t), 2.17(2H, t), 1.73(2H, q)

Comnound V—Anal. Calcd for $C_{17}H_{17}NO_5$: C, 64.74, H, 5.45, N, 4.44 Found: C, 64.11, H, 5.46, N, 4.21. ¹H NMR (300 MHz, D₂O): δ7.6 (1H,d), 7.35 (2H,d), 7.15 (2H,m), 6.05 (1H,d), 2.5 (2H,m), 2.1 (2H,t), 1.7 (2H,m)

Compound X—Anal. Calcd for $C_{23}H_{29}NO_3$: C, 75.16, H, 7.97, N, 3.79 Found: C, 74.90, H, 8.19, N, 3.38. ¹H NMR (300 MHz, CDCL₃): δ7.35 (2H,d), 7.27 (2H,d), 7.15 (2H,d), 6.95 (2H,d), 3.7 (1H,q), 2.6 (2H,t), 2.5 (2H,d), 2.35 (2H,t), 1.9 (3H,m), 1.6 (3H,d), 0.9 (6H,d)

Compound XVIII—¹H NMR (300 MHz, DMSO-d₆): δ12.1 (1H,s), 10.5 (1H,s), 8.2 (1H,t), 8.0 (2H,m), 7.7 (3H,d), 7.6 (3H,d), 7.2 (2H,t), 3.3 (1H,m), 2.6 (2H,t), 2.2 (2H,t), 1.8 (2H,t)

Compound XXII—Anal. Calcd for $C_{20}H_{23}NO_3$: C, 73.82, H, 7.12, N, 4.30 Found: C, 73.53, H, 7.07, N, 4.28. ¹H NMR (300 MHz, DMSO-d₆): δ12.0 (1H,s), 10.0 (1H,s), 7.6 (2H,m), 7.4 (4H,m), 7.2 (1H,d), 7.0 (2H,q), 3.55 (1H,t), 2.5 (4H,m), 2.2 (2H,q), 2.0 (1H,m), 1.7 (3H,m), 0.9 (3H,t)

Compound XXV—Anal. Calcd for $C_{18}H_{18}NO_3F$: C, 68.56, H, 5.75, N, 4.44 Found: C, 68.18, H, 5.63, N, 4.20. ¹H NMR (300 MHz, DMSO-d₆): δ12.1 (1H,s), 10.1 (1H,s), 7.5 (2H,m), 7.35 (2H,m), 7.1 (4H,m), 3.6 (2H,s), 2.5 (2H,t), 2.2 (2H,t), 1.75 (2H,m)

Compound XXVI—¹H NMR (300 MHz, D₂O): δ7.21(2H, d), 7.15(2H, d), 2.51(2H,t), 2.45(1H, m), 2.10(2H, t), 1.9–1.3(14H, m)

Compound XXVII—¹H NMR (300 MHz, DMSO-d₆): δ9.75 (1H,s), 7.5 (2H,d), 7.1 (2H,d), 2.5 (3H,q), 2.05 (3H,t), 1.6 (10H,m), 1.1 (5H,m), 0.8 (3H,t)

Compound XXVIII—¹H NMR (300 MHz, DMSO-d₆): δ9.82(1H, s), 7.49(2H, d), 7.06(2H,d), 2.48(2H, t), 2.32 (1H, m), 2.09(2H, t), 1.71(8H, m), 1.29(6H, m)

Compound XXIX—¹H NMR (300 MHz, DMSO-d₆): δ10.0 (1H,s), 7.5 (2H,d), 7.05 (2H,d), 2.5 (3H,m), 2.15 (2H,d), 1.85 (2H,t), 1.65 (8H,m), 1.2 (3H,m), 1.9(2H,q)

Compound XXX—¹H NMR (300 MHz, DMSO-d₆): δ 9.85 (1H,d), 7.5 (2H,d), 7.05 (2H,d), 2.45 (3H,m), 1.9 (2H,t), 1.7 (6H,m), 1.4 (4H,m), 0.9 (3H,dd)

Compound XXXIII—¹H NMR (300 MHz, DMSO-d₆): δ11.95(1H, s), 2.2(2H, m), 1.8(2H, m), 1.4(10, br m), 0.83(3H, d)

Compound XXXIV—Anal. Calcd for $C_{15}H_{19}NO_3$: C 68.96, H 7.26, N5.36, Found: C 68.75, H 7.24, N 5.30. ¹H NMR (300 MHz, D₂O): δ7.71 (2H, d), 7.33(2H, d), 2.06(2H, d), 1.52(6H, m), 1.01(3H, m), 0.84(2H, m)

Compound XXXV—Anal. Calcd for $C_{14}H_{10}NO_3Cl$: C, 60.96, H, 3.63, N, 5.08 Found: C, 60.42, H, 3.64, N, 4.94. ¹H NMR (300 MHz, DMSO-d₆): δ10.85 (1H,s), 7.95 (2H,d), 7.85 (2H,d), 7.55 (4H,m)

Compound XXXVI—Anal. Calcd for $C_{16}H_{21}NO_3$: C 69.79, H 7.70, N 5.08, Found: C 69.38, H 7.85, N 4.85. ¹H NMR (300 MHz, DMSO-d₆): δ10.0)1H, s), 7.45(2H, d), 7.10 (2H, d), 3.18(2H, d), 2.15(2H, d), 1.67(6H, br m), 1.17 (3H, m), 0.95(2H,m)

Compound XXXVII—¹H NMR (300 MHz, DMSO-d₆): δ12.25(1H, s), 9.8(1H,s), 7.5(2H, d), 7.15(2H, d), 3.5(2H, s), 2.3(1H, m), 1.8(4H, m), 0.3(6H, m)

Compound XXXVIII—Anal. Calcd for $C_{17}H_{15}NO_3$: C, 72.58, H, 5.39, N, 4.98 Found: C, 72.34, H, 5.21, N, 4.93. ¹H NMR (300 MHz, DMSO-d₆): δ10.2 (1H,s), 7.6 (5H, m), 7.4 (3H,q), 7.2 (2H,d), 6.85 (1H,d), 3.5 (2H,s)

Compound XL—¹H NMR (300 MHz,DMSO-d₆): δ8.6 (1H, m), 7.8 (2H,m), 7.25 (5H,m), 7.1 (2H,dd), 4.25 (2H,d), 3.5 (2H,s)

Compound XLI—Anal. Calcd for $C_{15}H_{13}NO_3$. 0.27 H2O: C, 70.57, H, 5.14, N, 5.49 Found: C, 69.24, H, 5.48, N, 5.37. ¹H NMR (300 MHz, DMSO-d₆): δ10.25 (1H,s), 8.0 (2H,d), 7.7 (2H,d), 7.55 (3H,m), 7.25 (2H,d), 3.5 (2H,s)

Compound XLII—¹H NMR (300 MHz, DMSO-d₆): δ 11.89 (1H, s), 7.58 (1H,s), 2.95(2H, t), 2.16(3H, m), 1.73(2H, t), 1.40(14H, m), 1.20(2H, t)

EXAMPLE 2

Compound IX was prepared as follows:

A solution of 4-phenylbutyryl chloride (10.20 g, 56 mmol) in tetrahydrofuran (30 mL) was added dropwise to a mixture of 4-(4-aminophenyl)butyric acid (10.00 g, 56 mmol, 1.0 equiv.), triethylamine (8.50 mL, 62 mmol, 1.1 equiv.) and tetrahydrofuran (100 mL) at 10° C. The reaction was stirred at 10° C. for 1 hour and 25° C. for 3 hours. The solvent was then evaporated, and the residue was dissolved in ethyl acetate (150 mL). After washing the ethyl acetate layer with aqueous hydrochloric acid (1 M, 3×100 mL) and water (2×100 mL), the organic layer was dried and evaporated. The resultant residue was recrystallized from acetonitrile-water to give IX as a pale yellow solid (11.69 g, 65%).

Properties are listed below.

¹H NMR (300 MHz, alkaline D₂O) δ: 7.05 (2H, m), 6.94 (4H, m), 6.85; (3H, m), 2.30 (4H, m) 2.01 (4H, m), 1.61 (4H, m). Anal. Calcd for $C_{20}H_{23}NO_3$: C, 73.81; H, 7.13; N, 4.30. Found: C, 73.53; H, 7.13; N, 4.25.

Similar procedures were used to prepare compounds I, III, IV, VII, VIII, XVII, XX, and XXI.

Properties are listed below.

Compound I—¹H NMR (300 MHz, D₂O): δ7.75 (2H,q), 7.55 (1 H,m), 7.45 (2H,m), 7.35 (2H,dd), 7.2 (2H,dd), 2.55 (2H,m), 2.1 (2H,t), 1.75 (2H,m)

Compound III—Anal. Calcd for $C_{17}H_{16}NO_3Cl$: C, 64.26, H,5.07, N,4.41 Found: C, 63.29, H, 5.12, N, 4.19. ¹H NMR (300 MHz, DMSO-d₆): δ12.1 (1H,s), 10.4 (1H,s), 7.7 (2H,d), 7.6 (2H,d), 7.45 (2H,m), 7.2 (2H,q), 2.6 (2H,m), 2.2 (2H,m), 1.8 (2H,m)

Compound IV—Anal. Calcd for $C_{17}H_{16}NO_3F$: C, 67.76, H, 5.35, N, 4.65 Found: C, 67.15, H, 5.33, N, 4.46. ¹H NMR (300 MHz, DMSO-d₆): δ12.05 (1H,s), 10.35 (1H,s), 7.6 (4H,m), 7.3 (2H,q), 7.15 (2H,q), 2.6 (2H,t), 2.2 (2H,t), 1.8 (2H,m)

Compound VII—¹H NMR (300 MHz, D₂O): δ 7.12(3H, m), 6.88(2H, s), 6.67(5H, br m), 6.26(1H, d), 2.18(2H, t), 1.96(2H, t), 1.50(2H, q)

Compound VIII—¹H NMR (300 MHz, D₂O): δ6.9 (9H,m), 2.6 (2H,t), 2.3 (4H,t), 2.0 (2H,q), 1.6 (2H,m)

EXAMPLE 3

Compound XXIV was prepared as follows:

N-hydroxysuccinamide (8.86 g, 77.00 mmol, 1.1 equiv.) and dicyclohexylcarbodiimide (15.88 g, 77.00 mmol, 1.1 equiv.) were added to a solution of 3-(4-fluorobenzoyl)

propionic acid (13.73 g, 70.00 mmol, 1 equiv.) in dimethylformamide (250 mL). The reaction was stirred at 25° C. under nitrogen for 12 hours. The solution was diluted with water (500 mL) and extracted with chloroform (250 mL). The organic layer was dried and filtered. Glacial acetic acid (5 mL) was added to the filtrate, and this mixture stirred for 1 hour. The resulting chloroform solution was washed with sodium bicarbonate (250 mL) and water (250 mL) and dried over magnesium sulfate. After filtration, 4-(4-aminophenyl) butyric acid (12.5 g, 70.00 mmol, 1 equiv.) and triethylamine (16 mL) were added to the filtrate. The resulting mixture was stirred at 25° C. overnight, and it was then acidified with hydrochloric acid (250 mL) and lyophilized to yield XXIV as a white solid. (3.50 g, 14%).

Properties are listed below.

$^1$H NMR (300 MHz, DMSO-$d_6$) δ: 12.05 (H, br s), 9.95 (1H, s), 8.10; (2H, t), 7.50 (2H, d), 7.35 (2H, t), 7.10 (1H, d), 2.70 (2H, t), 2.20 (2H, t), 1.75 (2H, m). Anal. Calcd for $C_{20}H_{20}NO_4F$: C, 67.02; H, 5.62; N, 3.90. Found: C, 67.08; H, 5.60; N, 3.86.

Similar procedures were used to prepare compound XLIII and XLIV.

Properties are listed below.

Compound XLIII—Anal. Calcd for $C_{22}H_{27}NO_3$ 0.083 H2O: C, 74.44, H, 7.73, N, 3.95 Found: C, 73.96, H, 7.73, N, 4.26. $^1$H NMR (300 MHs, DMSO-$d_6$): δ12.71 (1H,s), 8.2 (1H,q), 7.1 (9H,m), 4.4 (1H,m), 3.6 (1H,m), 3.0 (1H,m), 2.85 (1H,m), 2.4 (1H,q), 1.8 (1H,m), 1.3 (2H,d), 1.15 (1H,d), 0.85 (6H,d)

Compound XLIV—Anal. Calcd for $C_{22}H_{17}NO_4F_2$: C, 66.49, H, 4.32, N, 3.53 Found: C, 66.14, H, 4.29, N, 3.33. $^1$H NMR (300 MHz, DMSO-$d_6$): δ8.05 (1H,s), 7.5(2H, m), 7.35 (1H,m), 7.2(7H,m), 7.0 (1H,d), 4.7 (1H,m), 3.2 (1H,dd), 3.05 (1 H, m)

EXAMPLE 4

Compound XXXII was prepared as follows:

1-oxaspiro(2.5)octane (3.76 g, 33.48 mmol, 1.2 equiv.) and aluminum chloride (0.36 g, 2.70 mmol, 0.1 equiv.) were added to a suspension of 4-(4-aminophenyl)butyric acid (5.00 g, 27.90 mmol, 1 equiv.) in toluene (100 mL). The mixture was refluxed under argon overnight. After being cooled to room temperature, the toluene was filtered, and the residue was washed with ethyl acetate (ca. 100 mL). The combined filtrate was evaporated to yield a brown gum. The gum was dissolved with ethyl acetate (250 mL). It was then washed with water (3×100 mL) and dried. After removal of the solvent, the residue was purified by column chromatography (30% to 70% ethyl acetate/hexanes), and the collected product was recrystallized from ethyl acetate-hexanes to give XXXII as yellow solid (0.8 g, 10%).

Properties are listed below.

$^1$H NMR (300 MHz, DMSO-$d_6$) δ: 6.85 (2H, d, J=8.4 Hz), 6.53 (2H, d, J=8.4 Hz), 5.00 (1H, br s), 2.88 (2H, s), 2.39 (2H, t, J=7.2 Hz), 2.15 (2H, t, J=7.4 Hz), 1.69 (2H, m), 1.45 (10H, m). Anal. Calcd for $C_{17}H_{25}NO_3$: C, 70.07; H, 8.65; N, 4.81. Found: C, 70.20; H, 8.69; N, 4.67.

EXAMPLE 5

Compound XXXIX was prepared as follows:

N-hydroxysuccinimide (7.72 g, 67.50 mmol, 1.1 equiv.) and dicyclohexylcarbodiimide (13.96 g, 67.50 mmol, 1.1 equiv.) were added to a solution of N-(2-phenylbutyryl)-4-(aminophenyl)butyricacid (20.00 g, 61.40 mmol, 1.0 equiv.) in tetrahydrofuran (400 mL). The reaction was stirred overnight at 25° C. The urea formed was removed by filtration. Glacial acetic acid (5 mL) was added to the filtrate and stirred for 2 hours. The solvent was then evaporated to yield an oil. The oil was redissolved in chloroform (300 mL), and the resultant solution was washed successively with saturated sodium bicarbonate (2×200 mL) and water (200 mL). The combined aqueous layers were extracted with chloroform (100 mL) to give a filtrate (a total volume of 500 mL) containing the Osu ester of N-(2-phenylbutyryl)-4-(4-aminophenyl)butyric acid.

A mixture of phenylglycine O-methylester hydrochloride (12.40 g, 61.40 mmol, 1.0 equiv.) and triethylamine (35 mL) in chloroform (100 mL) was charged to an addition funnel. The mixture was added dropwise to the chloroform solution of the Osu ester prepared above. The reaction was stirred at 25° C. for 24 h. The resulting solution was washed with aqueous hydrochloric acid (2×500 mL) and water (500 mL). The aqueous layer was back extracted with chloroform (50 mL). The combined chloroform layers were dried and evaporated to yield an oil. Aqueous sodium hydroxide (2 M, 200 mL) was added to the oil, and the mixture was heated to 100° C. for 2 h. After being cooled to room temperature, the solution was acidified with hydrochloric acid (2 M) to pH 2.5. The precipitate was filtered, washed with hydrochloric acid (100 mL) and water (100 mL) to give XXXIX as an off white solid (15.2 g, 54%).

Properties are listed below.

$^1$H NMR (300 MHz, DMSO-$d_6$) δ: 12.70 (1H, br s), 10.00 (1H, s), 8.55 (1H, d), 7.50 (2H, d), 7.33 (10H, m), 7.06 (2H, d), 5.32 (1H, d), 3.54 (1H, m), 2.49 (2H, overlapped with DMSO), 2.16 (2H, m), 2.05 (1H, m), 1.73 (3H, m). 0.83 (3H, t). Anal. Calcd for $C_{28}H_{30}N_2O_4$: C, 73.30; H, 6.61; N, 5.73; Found: C, 72.54; H, 6.60; N, 5.73.

EXAMPLE 6

In Vivo Evaluation of Interferon in Rats

Dosing compositions were prepared by mixing the modified amino acid compounds and interferon α2 as listed in Table 1 below in a Trizma® hydrochloride buffer solution (Tris-Hcl) at a pH of about 7–8. Propylene glycol (0–25%) was added as a solubilizing agent, if necessary.

Rats were orally or intraduodenally (ID) administered the dosing compositions, and delivery was evaluated by an ELISA assay for human interferon α-2b.

Results are illustrated in Table 1 below.

TABLE 1

Oral Delivery of Interferon

| Carrier | Carrier Dose (mg/kg) | Interferon Dose (μg/kg) | Mean Peak Serum Levels of Interferon (ng/mL) |
|---|---|---|---|
| XXVI | 300 | 1000 | 6710 +/− 6658 |
| XXXVII | 160 | 1000 | 1025 +/− 276 |
| XXVII | 300 | 1000 | 3642 +/− 5895 |
| XXXIV | 400 | 1000 | 11341 +/− 8793 |
|  | 400 | 500 | 565 +/− 515 |
| XXXIV (ID) | 400 | 100 | 1775 +/− 1023 |
| XXIX | 600 | 100 | 3510 +/− 2171 |
| I | 300 | 1000 | 10972 +/− 3790 |
| I (ID) | 250 | 50 | 843 +/− 669 |
| I | 80 | 250 | 1369 +/− 1164 |
| VI | 300 | 1000 | 8213 +/− 3077 |
| VI | 600 | 1000 | 8428 +/− 5001 |
| VI (ID) |  | 1000 | 15469 +/− 6712 |
| XXXVI | 400 | 1000 | 43961 +/− 14910 |

TABLE 1-continued

Oral Delivery of Interferon

| Carrier | Carrier Dose (mg/kg) | Interferon Dose (μg/kg) | Mean Peak Serum Levels of Interferon (ng/mL) |
|---|---|---|---|
| XIV | 800 | 1000 | 5518 +/− 2718 |
| VII | 600 | 1000 | 5568 +/− 3771 |
| XXVII | 300 | 1000 | 41966 +/− 19688 |
| VIII | 300 | 1000 | 1753 +/− 1529 |
| XVIII | 300 | 1000 | 19809 +/− 26107 |
| XXX | 300 | 1000 | 3910 +/− 3221 |
| XL | 300 | 1000 | 12661 +/− 10933 |
| none | 0 | 1000 | 688 +/− 173 |

EXAMPLE 7

In Vivo Evaluation of Salmon Calcitonin in Rats

Dosing compositions were prepared and dosed using the modified amino acid compound carriers and salmon calcitonin as listed in Table 2 below. The concentration of calcitonin in each composition was 2.5 μg/ml. Each rat was administered 2 m/kg of dosing composition.

Blood samples were collected serially from the tail artery. Serum calcium was determined by testing with a Calcium Keto (Sigma Chemical Co.—St. Louis, Mo.).

Results are illustrated in Table 2 below.

EXAMPLE 8

In Vivo Evaluation of Salmon Concentration in Rats

A dosing composition was prepared using 400 mg of compound VI with 2.9 ml of 25% aqueous propylene glycol. The resultant solution was stirred, and the pH was adjusted to 7.2 with sodium hydrochloride (1.010). Water was added to bring the total volume to 2.0 ml and a final modified amino acid concentration of 200 mg/ml. Salmon calcitonin (10 mg) was added.

This composition was dosed as described in Example 7 above.

Results are illustrated in Table 2 below.

TABLE 2

Oral Delivery of Calcitonin

| Carrier | Carrier Dose (mg/kg) | Dose Drug (μg/kg) | Mean Peak Serum Levels of Calctonin |
|---|---|---|---|
| XXVI | 10 | 300 | −18 +/− 6 |
| XXVIII | 10 | 200 | −14 +/− 6 |
| I | 10 | 200 | −16 +/− 8 |
| VII | 10 | 200 | −13 +/− 8 |
| VI | 10 | 200 | −29 +/− 14 |
|  | 30 | 10 | −13 +/− 4 |
|  | 10 | 30 | −24 +/− 9 |

EXAMPLE 9

In Vivo Evaluation of Recombinant Human Growth Hormone (rhGh) in Rats

Dosing compositions were prepared with modified amino acids in a phosphate buffer at a pH of about 7–8 and rhGH as listed in Table 3 below.

Rats were administered the compositions by oral gavage, intraduodenal administration (ID), or colonic administration (IC).

Results are illustrated in Table 3 below.

TABLE 3

Oral Delivery of rhGH

| Carrier | Carrier Dose (mg/mL) | Dose Drug (mg/mL) | Mean Peak Serum Levels of rhGH (ng/mL) |
|---|---|---|---|
| XXVI | 500 | 6 | −127 +/− 40 |
| XXVII | 500 | 6 | −64 +/− 7 |
| VI | 150 | 6 | −33 +/− 13 |
| VI (ID) | 200 | 3 | −103 +/− 85 |
| VI (IC) | 50 | 1.5 | −98 +/− 19 |
| II | 400 | 6 | 55 +/− 36 |
| XXX | 400 | 6 | 66 +/− 37 |
| XLV | 400 | 6 | 28 +/− 9 |
| IV | 300 | 6 | 42 +/− 29 |
| XLII | 300 | 6 | 63 +/− 45 |
| X | 250 | 6 | 37 +/− 12 |
| XXXII | 200 | 6 | 44 +/− 36 |
| none | 0 | 6 | <10 |

EXAMPLE 10

In Vivo Evaluation of Heparin in Rats 900 mg of modified amino acid were dissolved in 3 ml of propylene glycol, and 0.299 gram of sodium heparin was dissolved in 3 ml of water. The two solutions were mixed by vortex. Sodium hydrochloride was added to the resultant mixture until a solution was obtained. The pH was then adjusted to 7.4±0.5 with concentrated hydrochloric acid. The final solution was sonicated at 40° C. for 30 minutes to yield a dosing solution.

The dosing solution was administered by oral gavage to fasted rats.

Blood samples were collected by cardiac puncture following the administration of ketamine (44 mg/kg). Heparin activity was determined by utilizing the activated partial thromboplastin time (APTT) according to the method of Henry, J. B., *Clinical Diagnosis and Management by Laboratory Methods*; Philadelphia, Pa.; W B Saunders (1979).

Results are illustrated in Table 4 below.

TABLE 4

Oral Delivery of Heparin

| Carrier | Mean Peat APTT (sec) | # Animals Responding |
|---|---|---|
| XXI | 166 +/− 35 | 5/5 |
| IX | 102 +/− 33 | 34/35 |
| VI | 96 +/− 29 | 10/10 |
| XLI | 90 +/− 49 | 5/5 |
| XXXV | 73 +/− 16 | 4/4 |
| VII | 52 +/− 24 | 17/20 |
| XV | 67 +/− 30 | 4/5 |
| XX | 59 +/− 42 | 4/4 |
| VII | 58 +/− 28 | 14/15 |
| XLII | 45 +/− 14 | 5/5 |
| XXXIII | 44 +/− 28 | 12/20 |
| XXVII | 44 +/− 15 | 18/20 |
| V | 42 +/− 16 | 4/5 |
| III | 41 +/− 18 | 8/10 |
| II | 41 +/− 24 | 3/5 |
| XXXIX | 40 +/− 17 | 5/10 |
| XIX | 37 +/− 11 | 4/5 |
| XXII | 36 +/− 19 | 6/11 |
| XXVIII | 35 +/− 9 | 3/5 |
| none | 20.7 +/− 0.17 | 100/100 |

EXAMPLE 11

Low molecular weight heparin was dosed according to the method of Example 10.

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claims.

What is claimed is:

1. A composition comprising:
   (A) at least one active agent; and
   (B) a compound having the following formula

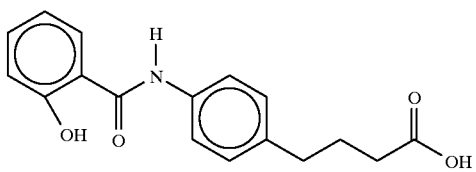

or a salt thereof.

2. A composition as defined in claim 1, wherein said active agent is selected from the group consisting of a biologically active agent, a chemically active agent, or a combination thereof.

3. A composition as defined in claim 2, wherein said biologically active agent comprises at least one peptide, mucopolysaccharide, carbohydrate, or lipid.

4. The composition as defined in claim 3, wherein said biologically active agent is selected from the group consisting of human growth hormone, bovine growth hormone, growth hormone-releasing hormone, an interferon, interleukin-II, insulin, heparin, low molecular weight heparin, calcitonin, erythropoietin, atrial naturetic factor, an antigen, a monoclonal antibody, samatostatin, adrenocorticotropin, gonadotropin releasing hormone, oxytocin, vasopressin, cromolyn sodium, vancomycin, parathyroid hormone, desferrioxamine (DFO), or any combination thereof.

5. A composition as defined in claim 4, wherein said biologically active agent comprises an interferon, interleukin-II, insulin, heparin, low molecular weight heparin, calcitonin, oxytosin, vasopressin, vancomycin, DFO, parathyroid hormone, and combinations thereof.

6. A composition as defined in claim 2, wherein said biologically active agent comprises parathyroid hormone.

7. A composition as defined in claim 2, wherein said biologically active agent comprises recombinant human growth hormone.

8. A composition as defined on claim 2, wherein said biologically active agent comprises interferon.

9. A composition as defined in claim 2, wherein said biologically active agent comprises heparin.

10. A composition as defined in claim 2, wherein said biologically active agent comprises low molecular weight heparin.

11. A composition as defined in claim 1, wherein said compound is included in a poly(amino acid).

12. A composition as defined in claim 1, wherein said compound is included in a polypeptide.

13. A dosage unit form comprising:
    (A) a composition as defined in claim 1; and
    (B) (a) an excipient
        (b) a diluent,
        (c) a disintegrant,
        (d) a lubricant,
        (e) a plasticizer,
        (f) a colorant,
        (g) a dosing vehicle, or
        (h) any combination thereof.

14. A dosage unit form as defined in claim 13, wherein said active agent is selected from the group consisting of a biologically active agent, a chemically active agent, or a combination thereof.

15. A dosage unit form as defined in claim 13, wherein said biologically active agent comprises at least one peptide, mucopolysaccharide, carbohydrate, or lipid.

16. A dosage unit form as defined in claim 15, wherein said biologically active agent is selected from the group consisting of human growth hormone, bovine growth hormone, growth hormone-releasing hormone, an interferon, interleukin-II, insulin, heparin, low molecular weight heparin, calcitonin, erythropoietin, atrial naturetic factor, an antigen, a monoclonal antibody, samatostatin, adrenocorticotropin, gonadotropin releasing hormone, oxytocin, vasopressin, cromolyn sodium, vancomycin, parathyroid hormone, desferrioxamine (DFO), or any combination thereof.

17. A dosage unit form as defined in claim 16, wherein said biologically active agent comprises an interferon, interleukin-II, insulin, heparin, low molecular weight heparin, calcitonin, oxytosin, vasopressin, vancomycin, DFO, parathyroid hormone, and combinations thereof.

18. A dosage unit form as defined in claim 13, wherein said biologically active agent comprises parathyroid hormone.

19. A dosage unit form as defined in claim 13, wherein said biologically active agent comprises recombinant human growth hormone.

20. A dosage unit form as defined on claim 13, wherein said biologically active agent comprises interferon.

21. A dosage unit form as defined in claim 13, wherein said biologically active agent comprises heparin.

22. A dosage unit form as defined in claim 13, wherein said biologically active agent comprises low molecular weight heparin.

23. A dosage unit form as defined in claim 13, comprising a tablet, a capsule, or a liquid.

24. A dosage unit form as defined in claim 23, wherein said dosing vehicle is selected from the group consisting of water, 1,2-propane diol, ethanol, or any combination thereof.

25. A method for administering a biologically-active agent to an animal in need of said agent, said method comprising administering orally to said animal a composition as defined in claim 2.

26. A compound having the formula

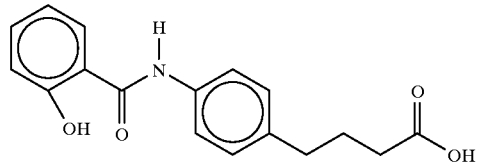

or a salt thereof.

27. A method for preparing a composition, said method comprising mixing:
    (A) at least one active agent;
    (B) at least one carrier compound as defined in claim 26; and
    (C) optionally, a dosing vehicle.

* * * * *